United States Patent [19]
Marchi-Lemann et al.

[11] Patent Number: 6,004,567
[45] Date of Patent: Dec. 21, 1999

[54] COSMETIC COMPOSITIONS COMPRISING NANOPIGMENTS

[75] Inventors: Patricia Marchi-Lemann, Paris; Annick Collette, Choisy le Roi; Myriam Mellul, L'Hay-les-Roses, all of France

[73] Assignee: L'Oreal, France

[21] Appl. No.: 08/819,083

[22] Filed: Mar. 18, 1997

[30] Foreign Application Priority Data

Mar. 20, 1996 [FR] France ................................. 96 03457
Apr. 17, 1996 [FR] France ................................. 96 04803

[51] Int. Cl.$^6$ ....................................................... A61K 7/48
[52] U.S. Cl. ............................ 424/401; 424/59; 424/63; 424/64; 424/69; 424/70.7; 514/937; 514/938
[58] Field of Search ............................... 424/401, 59, 63, 424/64, 69, 70.7; 514/937, 938

[56] References Cited

U.S. PATENT DOCUMENTS

| | | | |
|---|---|---|---|
| 5,616,331 | 4/1997 | Allard et al. | 424/401 |
| 5,643,557 | 7/1997 | Eteve et al. | 424/60 |

FOREIGN PATENT DOCUMENTS

| | | |
|---|---|---|
| 503922 | 9/1992 | European Pat. Off. . |
| 523294 | 1/1993 | European Pat. Off. . |
| 0 755 670 | 1/1997 | European Pat. Off. . |
| 61-257907 | 11/1986 | Japan . |
| 2-49719 | 2/1990 | Japan . |
| 6-199636 | 7/1994 | Japan . |
| 7-002615 | 1/1995 | Japan . |
| WO 95/09895 | 4/1995 | WIPO . |

*Primary Examiner*—Jyothsna Venkat
*Attorney, Agent, or Firm*—Finnegan, Henderson, Farabow, Garrett & Dunner, L.L.P.

[57] ABSTRACT

The subject of the invention is new cosmetic compositions, based on pigment nanoparticles and on fillers, which are completely transparent and free from whitening when they are applied on the skin, which possess sufficient UV screening properties for the addition of organic screening agents to be unnecessary, which are better dispersed than the compositions of the prior art and which are outstandingly stable. These compositions, when they are used in makeup, exhibit greater homogeneity of the colour and a colouring which is both transparent and more intense. The present invention also relates to methods of imparting these improved properties to makeup compositions.

25 Claims, No Drawings

COSMETIC COMPOSITIONS COMPRISING NANOPIGMENTS

The subject of the invention is new cosmetic compositions comprising pigment nanoparticles, fillers and a fatty binder, these compositions having improved optical and applicational properties and improved properties with respect to protection from UV radiation.

Cosmetic compositions (dispersions in an oil or water medium or water-in-oil (W/O) or oil-in-water (O/W) emulsions) comprising pigment nanoparticles, essentially titanium dioxide nanoparticles, and optionally fillers are known from Japanese Patent Nos. JP-06199636 and JP-072615 and European Patent No. EP-523294.

The decision to use titanium dioxide ($TiO_2$) nanoparticles is dictated by concern to obtain good protection against ultraviolet (UV) radiation without being bothered by the whitening characteristic of titanium dioxide of normal size. In other respects, it is known that compositions based on pigment nanoparticles are more heterogeneous than compositions based on pigments of normal size, due to poorer dispersion of the pigments; they are consequently more difficult to spread on the skin. The work described in the prior art has sought to solve this problem.

The known compositions of the prior art are not without disadvantages: A slight whitening can be observed when the amount of nanoparticles is high, in particular in the case of products of high protection against UV radiation. This defect is particularly noticeable in care products where the aesthetic qualities must be flawless. Some compositions solve this problem by combining an organic UV screening agent with $TiO_2$ nanoparticles, which makes it possible to use less $TiO_2$ in proportion. However, the daily topical use of compositions comprising one or a number of organic UV screening agents can be a source of allergies and can cause sensitization of the skin. In addition, in contrast to inorganic UV screening agents, organic UV screening agents are not completely stable over time, which causes a fall in their effectiveness and an increase in the risk of sensitization related to these products.

While compositions based on well-dispersed pigment nanoparticles are already known, in particular from the Japanese Patent Nos. JP-06199636 and JP-072615 and European Patent No. EP-523294, it has been possible, on the other hand, to observe, in these compositions, a reagglomeration of the pigment nanoparticles over time, the consequence of which is a rough feeling on spreading the composition on the skin and a deterioration over time in the aesthetic qualities of the product.

The aim of the present invention is to provide new cosmetic compositions based on pigment nanoparticles which are completely transparent and free from whitening when they are applied on the skin, which possess sufficient UV screening properties for the addition of organic screening agents to be unnecessary and which are better dispersed than the compositions of the prior art, this quality being maintained over time through the remarkable stability of these compositions.

The invention more particularly relates to cosmetic compositions comprising an amount of nanopigments greater than 2%, this amount being measured by weight with respect to the total weight of the composition. Below such a proportion of nanopigments, there are no problems of dispersion or of stability in the compositions comprising the nanopigments. In contrast, excessively low amounts of nanopigments do not make it possible to obtain satisfactory UV protection without the addition of other UV screening agents. Accordingly, the present invention is directed to solving the problems associated with compositions containing at least 2% by weight of nanopigments.

One subject of the invention is new cosmetic compositions comprising at least:
- 2% by weight of pigment in the form of nanoparticles which will be denoted nanopigment,
- a filler,
- a fatty binder, characterized in that:
- the concentration of pigment, i.e. nanopigment, by volume (CPV) of the combined nanopigments and fillers is less than or equal to the critical concentration of pigment by volume (CCPV), and
- the volume of the fillers Vf is greater than or equal to twice the volume of the nanopigments Vn.

The addition of fillers to the nanopigments under the conditions described above has the effect, with respect to the compositions known in the prior art, of improving the dispersion of the nanopigments, both at the time of the preparation of the composition and during its spreading; the stability of this dispersion is also improved. In addition, the optical qualities of the nanopigments are improved by the contribution of the intrinsic optical properties of the fillers. Finally, the compositions according to the invention, when they are used in makeup, exhibit improved aesthetic qualities which are reflected by greater homogeneity in the colour and a colouring which is both transparent and more intense, without deterioration in the qualities of this product over time.

The composition according to the invention thus comprises at least one filler, at least 2% of nanopigment and a fatty binder. The CPV of the fillers and nanopigments mixture is less than or equal to the CCPV.

If V denotes the volume of the combined fillers and nanopigments and V' denotes the volume of the non-volatile fraction of the fatty binder, the concentration of the pigment by volume, or CPV, of the combined nanopigments and fillers is defined by:

$$CPV = \frac{V}{V+V'} \times 100$$

It is recalled that the oil uptake is measured by determining the volume Vo of the non-volatile fraction of the fatty binder just necessary to fill in the interstices between the particles of the powder (filler plus nanopigment). The oil uptake can be measured, for example, according to the American standard ASTM D281-84, which is incorporated herein by reference. The critical concentration of pigment by volume (CCPV) is then defined by:

$$CCPV = \frac{V}{V+V_0} \times 100$$

The compositions according to the invention preferentially verify the relationship:

$CPV \leq CCPV/2$, and more preferentially still:

$CPV \leq CCPV/3$

Compositions are advantageously selected that verify:

$CPV = CCPV/3 \pm 10\%$

In the composition according to the invention, $Vf \geq 2Vn$ is also chosen.

The combination of these selection criteria makes it possible to obtain compositions with properties of UV protection, of transparency, of colouring and of ease of spreading which are greatly improved with respect to the prior art.

The shape of the nanopigment particles used in the present invention is unimportant. "Nanopigment" is preferably understood to mean a pigment in which the mean size of the unit particles ranges from 0.01 to 0.15 microns when these particles are substantially spherical; preferably they have a mean size ranging from 0.01 to 0.06 microns and more preferably from 0.01 to 0.03 microns. When the nanopigment particles are not spherical, they preferably have a longer side of less than 0.15 microns and more preferably ranging from 0.02 to 0.10 microns. Such nanopigments can be titanium oxide nanopigments corresponding to known titanium oxide nanopigments commonly used in the cosmetic field as screening agents.

The nanopigments used in the present invention can be selected from nanoparticles of inorganic pigments and of organic pigments, such as, for example, iron oxide, titanium dioxide, zinc oxide, bismuth oxychloride, calcium silicate, chromium oxide, chromium hydroxide, ammonium ferric ferrocyanide, ferric ferrocyanide, kaolin, manganese violet, ultramarine or carbon black nanoparticles and their mixtures. Metal oxide nanoparticles are preferably selected. These metal oxides are preferably selected from titanium, zinc and iron oxides, which form a barrier to UV radiation.

The fillers which can be used in the present invention are inorganic or organic fillers, preferably of large size, more preferably with a size greater than or equal to 10 microns. Mention may be made, as examples of inorganic fillers, of talc, silica, mica and boron nitride and, as examples of organic fillers, of nylon powder, silicone powder and poly (methyl methacrylate) powder. Lamellar fillers are preferably selected.

The fatty binder is selected in the usual way from oils and waxes of animal, vegetable or synthetic origin and their mixtures. In the case where the binder is solid at room temperature, such as, for example, in the case of waxes, the oil uptake is measured at the melting temperature of the binder.

Mention may be made, among the oils which can be used in the present invention, of mink oil, turtle oil, soybean oil, grape seed oil, sesame oil, maize oil, rapeseed oil, sunflower oil, cottonseed oil, avocado oil, olive oil, castor oil, jojoba oil, groundnut oil and hydrocarbon oils, such as liquid paraffins, squalane and petroleum jelly; esters, such as isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, di(2-ethylhexyl) succinate, diisostearyl malate, 2-octyldodecyl lactate, glyceryl triisostearate, and the like; silicone oils, such as polymethylsiloxanes, polymethylphenylsiloxanes, polysiloxanes modified with fatty acids, polysiloxanes modified with fatty alcohols, polysiloxanes modified with polyoxyalkylenes, fluorinated silicones, and the like; perfluorinated and organofluorinated oils; higher fatty acids, such as myristic acid, palmitic acid, stearic acid, behenic acid, oleic acid, linoleic acid, linolenic acid and isostearic acid, and higher fatty alcohols, such as cetanol, stearyl alcohol, oleyl alcohol, and the like; the waxes can be selected in particular from carnauba wax, candelilla wax, beeswax, spermaceti, microcrystalline waxes, lanolins, and the like.

The fatty binder can additionally contain volatile oils, which will evaporate on contact with the skin, but the presence of which in the cosmetic composition is useful because they facilitate the spreading of the composition during application on the skin. Such spreading agents, called volatile oils here, are generally oils having a saturated vapour pressure at 25° C. at least equal to 0.5 millibar (i.e. $0.5 \times 10^2$ Pa).

The volatile oils, when they are present, generally represent less than 10% by weight of the final composition and less than 20% by weight of the fatty binder. Mention will be made, among volatile oils which can be used in the present invention, for example, of silicone oils, such as hexamethyldisiloxane, cyclopentadimethylsiloxane and cyclotetramethylsiloxane, fluorinated oils, such as those sold under the name GALDEN (Montefluos), and isoparaffin oils, such as those which are sold under the name ISOPAR (E, G, L or H).

The cosmetic compositions according to the invention can be provided in the form of an anhydrous cast composition, of an oily dispersion, of a water-in-oil emulsion, of an oil-in-water emulsion, of a water-in-wax emulsion and of a wax-in-water emulsion. Wax-in-water and water-in-wax emulsions can only be prepared according to the present invention insofar as it is possible to measure, while hot, the CCPV of the nanopigments and fillers mixture for the wax or the mixture of waxes concerned; it is consequently preferable to select waxes or mixtures of waxes of low crystalline cohesion.

The compositions according to the invention generally comprise from 2 to 30% by weight of the nanopigments+ fillers mixture with respect to the remainder of the components. The nanopigments and fillers combination preferably represents from 5 to 15% by weight of the composition.

Preferably, when the composition according to the invention is a W/O or O/W emulsion, in order to optimize the dispersion of the nanopigments and of the fillers, the composition is prepared according to a process comprising at least two stages. The first stage comprises the preparation of a dispersion, from a homogeneous mixture of the nanopigments and fillers as defined above, in a portion of the fatty binder of the composition. The amount of the fatty binder to be used in this first stage of the process is evaluated by the person skilled in the art according to the amount of nanoparticles and fillers, so as to obtain, on conclusion of this first stage, a paste which is sufficiently supple to be able to be milled on a triple roll mill. This process is also a subject of the invention.

Preferably, the compositions according to the invention additionally comprise a dispersing agent, this agent contributing to better dispersion and better stability of the formula. Dispersing agents which can be used in the present invention are those corresponding to the formula X—CO—AR, in which A represents a divalent radical, R is a primary, secondary or tertiary amine or the salt of an amine with an acid or a quaternary ammonium and X represents a polyester residue, the X—CO— group being derived from a hydroxycarboxylic acid of formula $HOR_1COOH$ in which $R_1$ represents a saturated or unsaturated hydrocarbon group. Mention may be made, as examples of such dispersing agents, of derivatives of ricinoleic acid, of hydroxystearic acid or of the fatty acid from hydrogenated castor oil. Use may also be made of dispersing agents based on one or a number of polyester residues or based on the salts of a carboxylic acid or of a hydroxycarboxylic acid. The monoesters of fatty acid alkanolamides with carboxylic acids can also be used. For example, the alkanolamides can be selected from ethanolamine, propanolamine and aminoethylethanolamine. Dispersing agents can also be selected from those which are based on polymers or on copolymers of acrylic acid and of methacrylic acid, as well as those having an epoxy group in their base constituent, such as those prepared from ethoxylated phosphate esters.

The amount of dispersing agent used generally ranges from 5 to 35% by weight with respect to the weight of filler and nanopigment and preferably from 5 to 20% by weight with respect to the weight of filler and nanopigment.

The compositions according to the invention can also comprise the ingredients commonly used in cosmetics, among which there may be mentioned surfactants, whether non-ionic, cationic, anionic or amophoteric, fragrances or adjuvants which are usual in the cosmetics and dermatological fields, such as hydrophilic or lipophilic gelling agents, hydrophilic or lipophilic active principles, preservatives, antioxidants, solvents or colouring materials. The amounts of these various adjuvants are those conventionally used in the fields under consideration and, for example, from 0.01% to 20% of the total weight of the composition. These adjuvants, depending on their nature, can be introduced in the fatty phase, in the aqueous phase and/or in lipid spherules. Mention may be made, as examples of surfactants which can be used in the invention, of silicone-based emulsifiers and lipid emulsifiers, such as fatty alcohols, fatty acids, glycerol esters, sorbitan esters, methylglycoside esters and sucrose esters.

Mention may be made, as solvents which can be used in the invention, of lower alcohols, in particular ethanol and isopropanol, or propylene glycol.

Mention may be made, as hydrophilic gelling agents, of carboxyvinyl polymers (CARBOMER), acrylic copolymers, such as acrylate/alkyl acrylate copolymers, polyacrylamides, polysaccharides, such as hydroxypropyl cellulose or natural gums (xanthan), and clays and mention may be made, as lipophilic gelling agents, of modified clays, such as bentones, metal salts of fatty acids, such as aluminum stearates, hydrophobic silica, polyethylenes and ethyl cellulose.

Use may be made, as hydrophilic active principles, of proteins or protein hydrolysates, amino acids, polyols, urea, allantoin, sugars and sugar derivatives, water-soluble vitamins, starch, or bacterial or plant extracts, in particular of Aloe vera.

Use may be made, as lipophilic active principles, of tocopherol (vitamin E) and its derivatives, essential fatty acids, ceramides or essential oils.

It is possible to introduce into the compositions according to the invention, inter aeia, active agents intended in particular for the prevention and/or treatment of cutaneous conditions. Mention may be made, among these active agents, by way of example, of:

agents modulating cutaneous pigmentation and/or proliferation and/or differentiation, such as vitamin D and its derivatives, oestrogens, such as oestradiol, kojic acid or hydroquinone;

agents for combating free radicals, such as α-tocopherol or its esters, superoxide dismutases, certain metal chelating agents or ascorbic acid and its esters.

These compositions constitute in particular transparent tinted creams, creams and milks for antisun protection, foundations, lipsticks, eyeliners, mascaras, products for caring for the lips or cast powders.

The invention will be further described by the following examples, which are intended to be illustrative of the invention, but not limiting thereof.

EXAMPLES

The percentages given in the examples are percentages by weight.

Examples 1 to 16

Oil-in-water emulsions were prepared from:

| A1 | |
|---|---|
| glyceryl monostearate/polyethylene glycol stearate (50/50) | 2.10% |
| oxyethylenated sorbitan monostearate | 0.90% |
| cetyl alcohol | 0.50% |
| stearic acid | 1.50% |
| liquid petrolatum | z |
| propyl para-hydroxybenzoate | 0.20% |
| A2 | |
| titanium dioxide nanopigment | 5.00% |
| liquid petrolatum | x |
| filler | y |
| B | |
| water | q.s. for 100 |
| glycerol | 3.00% |
| propyl para-hydroxybenzoate | 0.25% |
| C | |
| cyclopentadimethylsiloxane | 3.00% |
| xanthan | 0.20% |
| carboxyvinyl polymer | 0.15% | where the nature of the filler, x, y and z were varied.

The various fillers used are described in Table 1:

TABLE 1

| Reference | Tradename | Producer | Nature | Size | Shape |
|---|---|---|---|---|---|
| C1 | Ceram Blanche 1 | SPCI | Boron nitride | 0.1 to 0.5 $\mu$m | Lamellar |
| C2 | Orgasol 2002 UDNatCos | Atochem | Nylon | 5 $\mu$m | Spherical |
| C3 | Ceram Blanche | SPCI | Boron nitride | 3 to 6 $\mu$m | Lamellar |
| C4 | Orgasol 2002 DNatCos | Atochem | Nylon | 11 $\mu$m | Spherical |
| C5 | Talc P3 | Nippon Talc | Talc | 1.8 $\mu$m | Lamellar |
| C6 | Tospearl 108 | Toshiba | Silicone | 0.8 $\mu$m | Spherical |
| C7 | Mica SFG70 | Aspanger | Mica | | Lamellar |
| C8 | Talc Luzenac | Luzenac | Talc | 15 $\mu$m | Lamellar |
| C9 | Microballoon Type H40 | Maprecos | Silica | 50 $\mu$m | Spherical |
| C10 | Silica Beads SB150 | Maprecos | Silica | 3–15 $\mu$m | Spherical |
| C11 | Tospearl 3120 | Toshiba | Silicone | 12 $\mu$m | Spherical |
| C12 | Micropearl M-100 | Seppic | PMMA | 10–20 $\mu$m | Spherical |

TABLE 1-continued

| Reference | Tradename | Producer | Nature | Size | Shape |
|---|---|---|---|---|---|
| C13 | Mica Concord 1000 | Sciama | Mica | 10 μm | Lamellar |
| C14 | SG Flake 3M | Maprecos | Silica | 3 μm | Lamellar |
| C15 | Covabead PMMA | Wackherr | PMMA | <5 μm | Spherical |
| C16 | Chemicelen | Sumitomo | Silica | 12 μm | Lamellar |

The percentage by volume of filler Vf is defined with respect to the percentage by volume of titanium dioxide Vn.

One or other of the values Vf/Nn=R1=0.84 and Vf/Vn=R2=2.81 was chosen.

From these percentages by volume, and knowing the relative densities of the fillers (approximately 2 g/cm$^3$) and of the titanium dioxide (3.97 g/cm$^3$), the value of y could easily be calculated.

The percentage by weight of oil x+z was calculated so that the composition verified CPV/CCPV=½ or CPV/CCPV=⅓.

The respective percentages x and z of the oil fractions introduced in A1 and A2 were adjusted in each case so that the phase A2 formed a paste which could be easily milled on a triple roll mill.

In a first step, the pigmentary paste A2 was prepared by introducing x % of liquid paraffin little by little into the homogeneous filler+titanium dioxide nanopigment mixture. This paste was milled three times on a triple roll mill. The mixture of the components of A1 was heated to 80° C. and A2 was introduced into this mixture with stirring, the A1+A2 mixture was then introduced into B at 80° C. and, finally, C was added at 40° C. to the rest of the composition. The mixture was allowed to homogenize with stirring and to return to room temperature. An antisun protection milk was obtained, the properties of which are reported in Table 2.

The references to the fillers C1 to C16 in Table 2 relate to the definitions given in Table 1.

The appearance of the compositions under the microscope was classified according to 5 categories numbered from 1 to 5:

1=poor dispersion, 5=very good dispersion. The viscosity was measured in poises. The smoothness, the whitening effect and the speed of disappearance of the whitening observed on spreading were evaluated with respect to a panel of 10 people; a mean value from 1 to 5 was given:

smoothness: 1=rough, 5=very smooth, whitening of the skin: 1=transparent, 5=white;

disappearance of the whitening: 1=very slow, 5=very fast.

We claim:

1. A cosmetic composition comprising at least one filler, at least one fatty binder and at least 2% by weight, with respect to the total weight of said composition, of at least one nanopigment, wherein:

the concentration of pigment by volume of said at least one nanopigment combined with said at least one filler is less than or equal to one half of the critical concentration of pigment by volume, and the volume of said at least one filler is greater than or equal to twice the volume of said at least one nanopigment, and wherein said at least one nanopigment is a pigment present in the form of nanoparticles and is dispersed in a portion of the fatty binder of the composition, and further wherein the cosmetic composition is in the form of a

TABLE 2

| Ex. No. | Filler | CPV/CCPV | Vf/Vn | ABSORPTION Visible 600 nm | UVA 350 nm | UVB 300 nm | TRANSMISSION Visible 600 nm | UVA 350 nm | UVB 300 nm | pH | Viscosity | Appearance | Smoothness | Whitening of the skin | Disappearance of the whitening |
|---|---|---|---|---|---|---|---|---|---|---|---|---|---|---|---|
| 1 | C1 | ½ | R1 | 0.1 | 0.4 | 0.5 | 75.8 | 45.6 | 31.7 | 7.95 | 5.62 | 2 | 3.6 | 4.05 | 2.25 |
| 2 | C2 | ½ | R1 | 0.1 | 0.4 | 0.5 | 78.2 | 44.6 | 32.7 | 8 | 4.2 | 2 | 3.4 | 3.4 | 3.1 |
| 3 | C4 | ⅓ | R2 | 0.3 | 1.3 | 1.6 | 50.8 | 5.8 | 2.6 | 8.09 | 14 | 3 | 3.3 | 3.05 | 3.45 |
| 4 | C5 | ½ | R1 | 0.2 | 0.6 | 0.8 | 67.3 | 26.6 | 15.3 | 7.99 | 6 | 2 | 3.6 | 3.3 | 3.45 |
| 5 | C6 | ½ | R2 | 0.3 | 1.0 | 1.3 | 53.1 | 8.2 | 4.1 | 8.07 | 7.8 | 3 | 3.5 | 3.05 | 3.45 |
| 6 | C7 | ½ | R1 | 0.3 | 1.0 | 1.3 | 51.9 | 9.4 | 5.1 | 8 | 8.2 | 4 | 3.8 | 2.85 | 3.8 |
| 7 | C8 | ⅓ | R2 | 0.3 | 1.3 | 2.1 | 51.9 | 4.3 | 0.8 | 7.93 | 22.4 | 3 | 4.2 | 2.55 | 3.75 |
| 8 | C9 | ½ | R1 | 0.1 | 0.7 | 1.0 | 73.0 | 22.4 | 6.9 | 8.42 | 2.5 | 3 | 3.6 | 4.05 | 2.25 |
| 9 | C10 | ⅓ | R2 | 0.3 | 1.4 | 1.8 | 47.3 | 4.4 | 1.9 | 7.85 | 18.6 | 4 | 3.9 | 2.7 | 3.8 |
| 10 | C11 | ⅓ | R1 | 0.3 | 1.3 | 1.6 | 45.1 | 5.1 | 2.4 | 8.05 | 4.18 | 2 | 3.85 | 2.7 | 3.8 |
| 11 | C12 | ½ | R1 | 0.3 | 1.1 | 1.4 | 56.4 | 8.9 | 4.3 | 8.05 | 4.5 | 3 | 3.6 | 3.3 | 3.8 |
| 12 | C13 | ⅓ | R2 | 0.3 | 1.9 | 2.8 | 45.6 | 1.2 | 0.1 | 7.9 | 70 | 4 | 3.5 | 3.05 | 3.45 |
| 13 | C14 | ⅓ | R1 | 0.3 | 1.4 | 1.6 | 50.1 | 5.1 | 3.1 | 7.8 | 41.5 | 5 | 3.8 | 2.85 | 3.8 |
| 14 | C15 | ⅓ | R2 | 0.3 | 1.4 | 1.7 | 47.8 | 4.7 | 2.4 | 8.03 | 13.2 | 3 | 3.75 | 3.5 | 3.1 |
| 15 | C16 | ½ | R2 | 0.3 | 1.6 | 2.5 | 47.6 | 2.4 | 0.4 | 8.1 | 14.5 | 5 | 3.55 | 3.05 | 3.6 |

The absorption and the transmission of UV radiation at different wavelengths were analyzed by measuring the optical density with a Lambda 16 (Perkin Elmer) spectrophotometer on a 6 mg sample placed between two quartz slides, with a spreading of approximately 2 mg/cm$^2$.

water-in-oil emulsion, an oil-in-water emulsion, a wax-in-water emulsion, or a water-in-wax emulsion.

2. A composition according to claim 1, wherein said concentration of pigment by volume of said at least one nanopigment combined with said at least one filler is less than or equal to one third of the critical concentration of pigment by volume.

3. A composition according to claim 1, wherein said nanopigment particles are substantially spherical and have a mean size ranging from 0.01 to 0.15 microns.

4. A composition according to claim 3, wherein said nanopigment particles are substantially spherical and have a mean size ranging from 0.01 to 0.06 microns.

5. A composition according to claim 4, wherein said nanopigment particles are substantially spherical and have a mean size ranging from 0.01 to 0.03 microns.

6. A composition according to claim 1, wherein said nanopigment particles are not spherical and have a longer side of less than 0.15 microns.

7. A composition according to claim 6, wherein said nanopigment particles are not spherical and have a longer side of less than 0.2 to 0.10 microns.

8. A composition according to claim 1, wherein said at least one nanopigment is selected from nanoparticles of inorganic and organic pigments.

9. A composition according to claim 8, wherein said at least one nanopigment comprises nanoparticles of iron oxide, titanium dioxide, zinc oxide, bismuth oxychloride, calcium silicate, chromium oxide, chromium hydroxide, ammonium ferric ferrocyanide, ferric ferrocyanide, kaolin, manganese violet, ultramarine, carbon black or mixtures thereof.

10. A composition according to claim 1, wherein said at least one nanopigment is a metal oxide.

11. A composition according to claim 10, wherein said metal oxide is titanium oxide, zinc oxide iron oxide, or a mixture thereof.

12. A composition according to claim 1, wherein said at least one filler has a size greater than or equal to 10 microns.

13. A composition according to claim 1, wherein said at least one filler is talc, silica, mica, boron nitride, nylon powder, silicone powder or poly(methyl methacrylate) powder.

14. A composition according to claim 1, wherein said at least one filler is a lamellar filler.

15. A composition according to claim 1, wherein said at least one nanopigment and said at least one filler are together present in an amount ranging from 2 to 30% by weight, with respect to the total weight of the composition.

16. A composition according to claim 15, wherein said at least one nanopigment and said at least one filler are together present in an amount ranging from 5 to 15% by weight, with respect to the total weight of the composition.

17. A composition according to claim 1, wherein said at least one fatty binder further comprises at least one volatile oil.

18. A composition according to claim 1, further comprising a dispersing agent.

19. A composition according to claim 18, wherein said dispersing agent corresponds to the formula X—CO—AR, in which
A represents a divalent radical,
R is a primary, secondary, or tertiary amine, or the salt of an amine with an acid or a quaternary ammonium, and
X represents a polyester residue, the X—CO—group being derived from a hydroxycarboxylic acid of formula HO—$R_1$—COOH, in which $R_1$ represents a saturated or unsaturated hydrocarbon group.

20. A composition according to claim 18, wherein said dispersing agent is present in an amount ranging from 5 to 35% by weight with respect to the weight of said at least one filler and said at least one nanopigment.

21. A composition according to claim 20, wherein said dispersing agent is present in an amount ranging from 5 to 20% by weight with respect to the weight of said at least one filler and said at least one nanopigment.

22. A composition according to claim 1, wherein said composition is in the form of a transparent tinted cream, of a cream or of a milk for antisun protection, of a foundation, of a lipstick, of a product for caring for the lips, of a mascara, of an eyeliner or of a cast powder.

23. A method of imparting homogeneous color to a makeup composition, comprising the step of including in said makeup composition a composition according to claim 1.

24. A method of imparting intense coloring to a makeup composition, comprising the step of including in said makeup composition a composition according to claim 1.

25. A method of preparing a transparent makeup composition, comprising the step of including in said makeup composition a composition according to claim 1.

* * * * *